United States Patent [19]

Atsumi et al.

[11] Patent Number: 5,151,122
[45] Date of Patent: Sep. 29, 1992

[54] PROCESS FOR PRODUCING AN ANTIBACTERIAL CERAMIC MATERIAL

[75] Inventors: Kiminori Atsumi; Tomoki Saito; Masaaki Komori, all of Tokyo, Japan

[73] Assignee: Kabushiki Kaisha Sangi, Tokyo, Japan

[21] Appl. No.: 611,839

[22] Filed: Nov. 13, 1990

[30] Foreign Application Priority Data

Nov. 14, 1989 [JP] Japan ................................ 1-293992
Aug. 30, 1990 [JP] Japan ................................ 2-226738

[51] Int. Cl.$^5$ ................. C09K 3/00; C09D 5/16; A23L 1/20; A23L 1/31
[52] U.S. Cl. ...................... 106/35; 106/18.36; 424/602; 424/618; 424/630; 424/641; 424/421; 423/308; 423/311
[58] Field of Search ................... 106/35, 18.36; 501/1; 424/602, 618, 630, 641, 421; 423/308, 311

[56] References Cited

U.S. PATENT DOCUMENTS

| | | | |
|---|---|---|---|
| 4,448,758 | 5/1984 | Nagai et al. | 423/308 |
| 4,906,466 | 3/1990 | Edwards et al. | 424/421 |
| 4,911,849 | 1/1989 | Hagiwara et al. | 424/618 |
| 5,009,898 | 4/1991 | Sakuma et al. | 423/308 |

FOREIGN PATENT DOCUMENTS 169427 6/1985 Japan ................................. 424/618

Primary Examiner—William R. Dixon, Jr.
Assistant Examiner—C. Melissa Bonner
Attorney, Agent, or Firm—Finnegan, Henderson, Farabow, Garrett & Dunner

[57] ABSTRACT

An antibacterial ceramic material wherein at least one ceramic selected from the group consisting of hydroxyapatite, calcium phosphate, calcium hydrogen phosphate, calcium carbonate, calcium silicate and zeolite is made to absorb and tightly retain at least one liquified metal salt selected from the group consisting of salts of silver, copper and zinc, after which heat firing at elevated temperatures is performed.

4 Claims, No Drawings 5,151,122

PROCESS FOR PRODUCING AN ANTIBACTERIAL CERAMIC MATERIAL

BACKGROUND OF THE INVENTION

1. Field of the Invention

This invention relates to antibacterial ceramic materials which are shown to be highly safe and manageable powders which can be admixed with resins, fibers, papers, ceramics and the like. These ceramics have been made to absorb and carry tightly a metal ion or metal salt, namely at least one metal salt of silver, zinc and copper, after which the same ceramic is heat fired at elevated temperatures, preferably 800° C. or higher. The high temperatures cause the ceramic to undergo contraction and it is thereby treating the material in such a manner as to permanently lock-in the said metal ions or metal salts so that they will not desorb or elute into a contacting fluid.

2. Description of the Prior Art

It has long been known that metals selected from among silver, copper and zinc, as well as their metal ions and salts, exhibit a strong antibacterial property. Various processes have been proposed for utilizing this antibacterial property by providing a substrate, such as a textile or synthetic resin, with such a material by means of diffusion, adsorption or coating. However, since these metals exhibit poor dispersibility with respect to a substrate, it is difficult to disperse them in a substrate homogeneously, and therefore the article obtained tends to display a non-uniform quality and non-uniform antibacterial property. An article thus obtained by simply diffusing the metal salt in a substrate is such that the metal ion or metal salt elutes from the substrate in the presence of water. Consequently, the article suffers a decline in quality and antibacterial capability, and the eluted metal ion or metal salt can cause undesirable damage. In addition, for example, since salts such as silver salts readily change color when exposed to daylight, it is difficult to store them for long periods and articles to which these salts have been added may also undergo a change in color. Despite the fact that these metal ions or their salts are highly resistant to heat and possess a strong antibacterial property, the foregoing drawbacks preclude much use of these materials as antibacterial agents except in some very limited fields of application.

In recent years substances in which an ion exchanger is used as a carrier and the carrier undergoes an ion exchange with or absorption of the aforementioned metal ions or salts have been proposed as carriers that enable the antibacterial property of the metals, metal ions or metal salts to be utilized safely. For example, the specification of Japanese Patent Application Laid-Open (Kokai) No. 60-181002 discloses an antibacterial agent in which zeolite is made to undergo an ion exchange with these metal ions. By virtue of this ion exchange process, elution of the antibacterial metal ions into water is reduced, dispersibility in a substrate such as that of a textile, synthetic resin or the like is also improved, the drawbacks observed in the prior art when a metal, metal ion or salt is used as an antibacterial agent are therefore mitigated, and antibacterial metals can be utilized in comparative safety. However, in a process with an ion exchanger, such as zeolite, which is made to carry antibacterial metal ions by means of ion exchange, the amount of metal ions which can undergo the ion exchange is limited by the ion-exchange capacity of the carrier material and therefore it is necessary to use an ion exchanger having a large ion-exchange capacity in order to achieve a desired strong antibacterial property. A problem encountered however is that the types of ion exchangers that can be used are limited. In addition, the antibacterial metal ions carried on the ion exchanger as a result of the ion exchange cannot always be used with safety in any medium of choice because these metal ions may be released out of the carrier depending upon the particular type of carrier used. Further recently, in a zeolite antibacterial agent, obtained by an exchange of silver ions, discoloration has been shown to be reduced in comparison to a material in which a silver salt is simply adsorbed. However, since discoloration does occur with the passage of time, storage for long periods has proven difficult and articles to which this zeolite and metal salt has been added are likely to deteriorate owing to discoloration.

The specification of Japanese Patent Application Laid-Open No. 60-181002 discloses a method to heat treat the metal-ion exchanged into zeolite at a temperature of 340°–580° C., which is lower than that at which the zeolite would start to undergo thermal decomposition, with the purpose being to reduce the conversion of metal into metal oxide to limit the amount of gases evolved at the time of use. Consequently, when the metal-ion exchanged zeolite is used, depending on the conditions, use is facilitated since safety in terms of the composition has been enhanced somewhat in comparison with the metal-substituted zeolite that has not been heat treated. However there is no significant difference with regard to the release of metal ions and or discoloration with the passage of time. Moreover, if zeolite carrying silver is heat treated at a temperature of higher than 600° C., which is greater than the temperatures of 340°–580° C. mentioned in Japanese Patent Application Laid-Open No. 60-181002, colors of gray to black are produced owing to the action of the silver, and this prevents its use in many needed applications.

SUMMARY OF THE INVENTION

Accordingly, an object of the present invention is to provide an antibacterial ceramic material in which an antibacterial metal or metal ion will not elute into any contacting medium whatsoever, whereby restraint of use due to the metal or metal ion need not be given special thought.

Another object of the present invention is to provide an antibacterial ceramic material in which a comparatively large amount of antibacterial metal or metal salt is retained by absorption, or antibacterial metal ion is exchanged with ceramic material as a result of which the material exhibits superior antibacterial property safely and for an extended unknown period of time.

Another object of the present invention is to provide an antibacterial ceramic material in which an antibacterial metal and/or metal ion or salt can be absorbed or exchanged yet with excellent dispersibility in a substrate such as that of fiber, synthetic resin or the like and exhibit extremely high stability with respect to heat, and wherein the material will not change color even when stored for long periods.

As set forth above, antibacterial zeolite obtained by causing zeolite to undergo an ion exchange with an antibacterial metal ion is a relatively easy-to-use antibacterial agent having comparatively high stability. However, since the amount of metal ions that can be carried is influenced by the ion-exchange capability of the zeolite used, there is wide disiparity in the antibacterial performance obtained depending upon the type of zeolite used and the ion-exchange conditions. In addition, since the metal ion gradually elutes into a contacting medium, the antibacterial effectiveness gradually declines with prolonged use. Accordingly, the inventors of this process have carried out extensive research regarding the development of a process for producing an antibacterial ceramic material which is safe, highly antibacterial and extremely resistant to the decline in antibacterial effectiveness, wherein these features are achieved by retaining a large amount of antibacterial metal and/or metal ion and assuring that the metal or metal ion will not elute into a contacting medium, regardless of its type. As a result of this research, the inventors have succeeded in producing an antibacterial ceramic material that is highly desirable. Specifically, it has been found that an antibacterial metal and/or metal ion or salt can be made to bind exceptionally well to a ceramic with superior strength by causing an antibacterial metal ion or salt to be sufficiently absorbed on or exchanged with a ceramic by utilizing the fact that all ceramics are porous although to varying degress and have a strong tendency for such properties, and then subsequently drying and heat firing the ceramic, as a result of which the antibacterial metal or metal salt will not elute irrespective of the material in which it is treated. In accordance with this process, the amount of metal and/or metal salt retained is far greater than the amount of metal ion that can be borne by ion exchange alone. As a consequence, the antibacterial effectiveness of the antibacterial ceramic material obtained is much greater than that of a ceramic antibacterial agent obtained by ion exchange process alone, and therefore a smaller amount of the metal or metal ion addition can suffice. Since the binding between the ceramic and the antibacterial metal or metal ion is ever more strengthened by heat firing, elution of the metal ion is virtually undetectable in any contacting medium. This makes possible safe storage and use for long periods of time.

The carrier used in the present invention is one used generally as an absorbent. For example, it is possible to use alumina, silica gel, bentonite, acid clay or kieselguhr. However, since bentonite, acid clay and kieselguhr form glass when heat fired at elevated temperatures, these cannot be used in the form of a pulverulent body. Ceramics that are stable even when heated to 1200°–1300° C., such as alumina, silica, titanium dioxide and zirconium oxide, are not capable of retaining the metals strongly even though heat fired, and for this reason the metal ions can elute in large quantity. In the case where silver is used as the metal, the color of the powder also becomes gray to black, and in the case of silica, the color becomes yellowish brown. Such a ceramic is unattractive and is therefore difficult to use and hence has a very limited range of application. However, when silver is used with a ceramic, selected from the group consisting of zeolite and calcium compounds such as hydroxyapatite, calcium phosphate, calcium hydrogen phosphate, calcium metaphosphate, calcium carbonate and calcium silicate, and absorbed in a large amount and which then undergoes heat firing, it causes contraction of the ceramic when heated to and between 800°–1300° C. Consequently, the metal or metal ion can be held to much higher degrees and elution of the metal ion will not occur. Also in the case where silver is used as the metal or metal salt, the color of the powder remains white and therefore has no limitation upon the field of application. In the manufacturing process, the ceramic is made into fire powders of 100 μm or less.

In the prior art, where heat treating is carried out at between 340°–580° C., as in the aforementioned Japanese Patent Application Laid-Open No. 60-181002, the resulting composition is not significantly different from a non-heat treated one, and neither of the problems of elution of the metal ion nor discoloration with time can be completely prevented. If heat treating is carried out at a temperature higher than 600° C., the zeolite decomposes and the resulting color ranges from gray to black owing to the action of the silver. Heat treating at such temperatures therefore had not be considered. However, the present inventors have found that the color returns to white when zeolite, carrying a metal is heat fired at a temperature higher than 800° C., and that the metal ion or salt consequently will not elute from the zeolite. By virtue of this fact, safety is enhanced and the antibacterial property is retained ever for long periods, thereby greatly broadening the range of application. After the ceramic has been made to absorb an aqueous solution containing the antibacterial metal ion or salt, namely a salt of silver, copper or zinc, in accordance with an ordinary method, the treated ceramic is washed, dried and then heat fired. Though the firing temperature can be varied at will depending upon the type of ceramic used, a temperature as high as possible is preferred, and preferably a temperature above 800° C. Though heat firing can be performed at the temperature is up to the boiling point of silver, such heat firing would vaporize the metal. For this reason, heat firing should be carried out at a temperature of not more than 1300° C. Owing to such heat firing, the absorbed metal and/or metal ion will no longer elute even into a solvent if the ceramic is treated in a solvent. The amount of metal and metal ion absorbed is selected depending upon the ceramic carrier used, type of metal salt selected, its concentration and range of temperature. However, since there are still instances where metal oxides may separate out, the amount of metal and/or metal ion absorbed should be less than that of over saturation, preferably 15-0.0001 wt.—% by weight with respect to the ceramic.

· The antibacterial ceramic material thus obtained is such that the amount of metal elution in water is less than the amount detectable, making usage safe, the antibacterial property is maintained virtually forever, and there is no discoloration and a superior antibacterial effect is obtained even by adding less than 50 wt.—%, preferably about 0.1 –10 wt.—%, to the ceramic carrier compared to otherwise formed material. In addition, the antibacterial property is not lost or impaired by subjection to heat, and the ceramic carrier is readily dispersed in a material. A molded article having a uniform antibacterial property is thus readily obtained if the ceramic carries is dispersed in a synthetic resin and the resin is then molded. When a pulverulent body, such as the material of this invention, is heat fired, this highly promotes binding into solid particles, and a reduction in the overall surface area of the pulverulent body, its porosity and virtually no water absorption has been verified. In the method of the present invention furthermore, heat firing has been shown to strengthen the bond between the ceramic and the absorbed metal and metal ion which reduces reactivity with water, and it is believed that no elution of the absorbed metal or metal salt into water will be detected.

Other features and advantages of the present invention will be apparent from the following description.

DESCRIPTION OF THE PREFERRED EMBODIMENT

Examples of the present invention will now be described in detail.

EXAMPLE 1

To 10 l of distilled water were added 1.0 kg of hydroxyapatite, 32 g of silver nitrate and 69 g of zinc nitrate, followed by stirring. This resultant state in dried cake like form, was washed thoroughly with distilled water, dried and a portion thereof was powdered to provide an antibacterial hydroxyapatite (1—1) containing approx 2% silver and about 1.5% zinc. The remaining portion was heat fired at 1200° C. and powdered to provide antibacterial hydroxyapatite (1-2) carrying approx 2% silver and about 1.5% zinc.

EXAMPLE 2

To 10 l of distilled water were added 1.0 kg of tricalcium phosphate, 30 g of silver nitrate and 45 g of zinc nitrate, followed by stirring. This resultant state in cake like form was washed thoroughly with distilled water, dried and a portion thereof was powdered to provide antibacterial tricalcium phosphate (2-1) containing approx 0.8% silver and about 1% zinc. The remaining portion was heat fired at 1100° C. and powdered to provide antibacterial tricalcium phosphate (2—2) carrying approx 0.5% silver and about 1% zinc.

EXAMPLE 3

To 10 l of distilled water were added 1.0 kg of calcium carbonate and 0.01 g of silver nitrate, which was followed by stirring. This state in cake like form was washed thoroughly with distilled water, dried and a portion thereof was powdered to provide antibacterial calcium carbonate (3-1) containing approx 0.001% silver. The remaining portion was heat fired at 800° C. and powdered to provide antibacterial calcium carbonate (3-2) carrying about 0.0001% silver.

EXAMPLE 4

To 10 l of distilled water were added 1.0 kg of calcium silicate, 180 g of silver nitrate and 200 g of copper nitrate, which was followed by stirring while boiling. This state in cake like form was washed thoroughly with distilled water, dried and a portion thereof was powdered to provide antibacterial calcium silicate (4-1) containing approx 10% silver and about 5% copper. The remaining portion was heat fired at 1200° C. and powdered to provide antibacterial calcium silicate (4-2) carrying approx 10% silver and about 5% copper.

EXAMPLE 5

Antibacterial zeolite available on the market carrying about 2% silver and about 1.5% zinc was used as a sample (5) for comparison purposes in the experiment cited hereinbelow.

EXAMPLE 6

To 10 l of distilled water were added 1.0 kg of zeolite, 32 g of silver nitrate and 46 g of zinc nitrate, which was followed by stirring. This state in cake like form was washed thoroughly with distilled water, dried and a portion thereof was powdered to provide antibacterial zeolite (6-1) containing approx 2% silver and about 1% zinc. The remaining portion was heat fired at 800° C. and powdered to provide antibacterial zeolite (6-2) carrying approx 2% silver and about 1% zinc.

EXAMPLE 7

Metal Ion or Salts Elution Experiment

The specimens 1—1 through 6-2 mentioned above were each added to an amount of 1 g to 100 ml of distilled water, followed by stirring for 30 min. By using an atomic-absorption spectrophotometer, the metal ions or salts in each resultant solution were measured and the amount of elution was determined.

|     | SILVER (ppm) | ZINC (ppm) | COPPER (ppm) |
| --- | --- | --- | --- |
| 1-1 | 0.5 | 0.2 | |
| 1-2 | <0.01 | <0.2 | |
| 2-1 | 5.0 | 0.4 | |
| 2-2 | <0.01 | <0.2 | |
| 3-1 | 0.02 | — | |
| 3-2 | <0.01 | — | |
| 4-1 | 2.3 | — | 0.9 |
| 4-2 | <0.01 | — | <0.1 |
| 5 | 0.9 | 1.2 | |
| 6-1 | 9.1 | 11.7 | |
| 6-2 | <0.01 | <0.2 | |

(The "<" symbol indicates less than the limit of detection.)

As indicated in the table above, elution of a metal can be prevented by heat firing the ceramic containing the metal.

EXAMPLE 8

Antibacterial Effectiveness Experiment

A solution of colon bacillus was added to a phosphate buffer solutions of physiological saline to which the samples of 1—1 through 2—2 and 4-1 through 5 had been added in an amount of 0.1 wt.—% each and the samples of 3-1, 3-2 in an amount of 50 wt.—% each. Antibacterial effectiveness against colon bacillus was then measured.

|     | 0 Hrs. | 24 Hrs. Later |
| --- | --- | --- |
| 1-1 | $2.9 \times 10^5$ | <1 |
| 1-2 | $2.9 \times 10^5$ | <1 |
| 2-1 | $2.9 \times 10^5$ | <1 |
| 2-2 | $2.9 \times 10^5$ | <1 |
| 3-1 | $2.9 \times 10^5$ | <1 |
| 3-2 | $2.9 \times 10^5$ | <1 |
| 4-1 | $2.9 \times 10^5$ | <1 |
| 4-2 | $2.9 \times 10^5$ | <1 |
| 5 | $2.9 \times 10^5$ | <1 |
| 6-1 | $2.9 \times 10^5$ | <1 |
| 6-2 | $2.9 \times 10^5$ | <1 |

The "<1" indication is based on the limit of bacteria measurement and means that bacteria were not detected.

EXAMPLE 9

Discoloration Experiment

White-colored antibacterial hydroxyapatite (1-2) and a white-colored antibacterial zeolite (5) as available on the market were placed in clear polystyrene bags, and the bags were let to stand in a room in indirect light storage situation. As a result, it was confirmed that the color of the antibacterial zeolite (5) available on the market changed to a somewhat yellowish color after half a year, and to a lemon yellow color after one year. (It was found that the powder on the very outer surface was a darker yellow than the powder in the center of the bag.) However, the antibacterial hydroxyapatite kept its white color and exhibited no discoloration even after one year. The antibacterial zeolite (6-2) prepared in accordance with the method of the present invention also maintained its white color and exhibited no discoloration in like fashion.

Thus, it is evident that the antibacterial ceramic material obtained in accordance with the present invention not only possesses an antibacterial effectiveness equivalent to that of conventional antibacterial zeolite but further also exhibits virtually no elution of the metal ion or metal salts and does not change color even over very long periods of time.

The antibacterial ceramic material according to the present invention is highly resistant to heat and exhibits excellent dispersibility and therefore can be used in a wide range of fields upon being added to a fiber, plastic, paper or ceramic etc. Since there is no detectable elution of metal or metal ion or metal salts, the antibacterial ceramic material of this invention can be used especially in fields that require a high level of safety, such as in the fields of cosmetics, pharmaceuticals, food packaging, medical instruments and biological materials. In particular, since there is no elution of metal or metal ion or metal salts and no decline in the antibacterial effectiveness even in boiling water, the antibacterial ceramic material of this invention can be used in packing materials that undergo boiling or steam sterilization or in water purifiers that employ hot water.

As many apparently widely different embodiments of the present invention can be made without departing from the spirit and scope thereof, it is to be understood that the invention is not limited to the specific embodiments thereof except as defined in the appended claims.

What is claimed is:

1. A method of preparing an antibacterial ceramic material comprising contacting at least one ceramic material selected from the group consisting of hydroxyapatite, calcium phosphate, calcium hydrogen phosphate, calcium carbonate, calcium silicate and zeolite with at least one aqueous metal salt selected from the group consisting of aqueous salts of silver, copper and zinc, and thereafter drying and heat firing the material to a temperature of from 800° C. to 1300° C.

2. The method of claim 1, wherein the ceramic is hydroxyapatite.

3. The method of claim 1 or 2 wherein the aqueous metal salt is a salt of silver and a salt of zinc.

4. The method of claim 3, wherein the salts are silver nitrate and zinc nitrate.

* * * * *